United States Patent [19]
Tada et al.

[11] Patent Number: 5,639,776
[45] Date of Patent: Jun. 17, 1997

[54] 4, 5-DIHYDROPYRAZOLE-5-THIONE DERIVATIVES AND MITICIDES COMPRISING THE SAME

[75] Inventors: Isao Tada, Itano-gun; Minoru Motoki, Naruto; Nobuyoshi Takahashi, Tokushima; Tetsuji Miyata, Itano-gun, all of Japan

[73] Assignee: Otsuka Kagaku Kabushiki Kaisha, Osaka, Japan

[21] Appl. No.: 702,671

[22] PCT Filed: Jan. 12, 1996

[86] PCT No.: PCT/JP96/00044

§ 371 Date: Sep. 11, 1996

§ 102(e) Date: Sep. 11, 1996

[87] PCT Pub. No.: WO96/21651

PCT Pub. Date: Jul. 18, 1996

[30] Foreign Application Priority Data

Jan. 12, 1995 [JP] Japan ................. 7-003388
Jan. 12, 1995 [JP] Japan ................. 7-003389
Sep. 28, 1995 [JP] Japan ................. 7-251034

[51] Int. Cl.$^6$ ............. A01N 43/40; A01N 43/56; C07D 231/18; C07D 401/04
[52] U.S. Cl. ............. 514/404; 546/276.1; 548/366.1; 548/370.4; 548/371.7; 548/357.5
[58] Field of Search ............. 546/276.1; 548/366.1; 514/404

[56] References Cited

PUBLICATIONS

Maquestiau et al, *Chemical Abstracts*, vol. 87 No. 2313q (1977).
la Cour et al, *Chemical Abstracts*, vol. 118 No. 138575 (1993).

*Primary Examiner*—Robert W. Ramsuer
*Attorney, Agent, or Firm*—Kubovcik & Kubovcik

[57] ABSTRACT

The object of the present invention is to provide a novel 4, 5-dihydropyrazole-5-thione derivative which exerts remarkably potent miticidal activity. The 4, 5-dihydropyrazole-5-thione derivative of the present invention is represented by the general formula

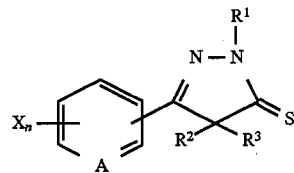

wherein $R^1$ represents a straight- or branched-chain alkyl group having 1 to 12 carbon atoms or the like; $R^2$ and $R^3$ represent a lower alkyl group or the like; X represents a halogen atom or the like, n is 0 or an integer of 1 to 3; and A represents —(C)— or —(N)—.

5 Claims, No Drawings

4, 5-DIHYDROPYRAZOLE-5-THIONE DERIVATIVES AND MITICIDES COMPRISING THE SAME

TECHNICAL FIELD

The present invention relates to novel 4, 5-dihydropyrazole-5-thione derivatives and to miticides comprising the same.

PRIOR ART

Of dihydropyrazolone derivatives, some are known as bioactive compounds, and several publications disclose such bioactivity of the compounds. For example, EP patent specification No. 23636 discloses compounds which exert insecticidal activity and Japanese Unexamined Patent Publication No. 213892/1993 discloses compounds which exert herbicidal activity. However, there has been no disclosure that 4, 5-dihydropyrazole-5-thione derivatives have bioactivity applicable to agriculture.

DISCLOSURE OF THE INVENTION

In view of the foregoing, the inventors conducted extensive research on dihydropyrazolone derivatives to develop compounds which exhibit excellent bioactivity applicable to agriculture and found that 4, 5-dihydropyrazole-5-thione derivatives represented by the following general formula (1) are novel compounds undisclosed in the publications and that although 4, 5-dihydropyrazol-5-one derivatives which are intermediates for synthesizing 4, 5-dihydropyrazole-5-thione derivatives do not have miticidal activity, 4, 5-dihydropyrazole-5-thione derivatives represented by the following general formula (1) have remarkably potent miticidal activity against various kinds of spider mites which adversely affect agriculture. The present invention was accomplished based on the above-mentioned findings.

In accordance with the present invention, there are provided a 4, 5-dihydropyrazole-5-thione derivative represented by the following general formula (1) and a miticide comprising the derivative as an active ingredient

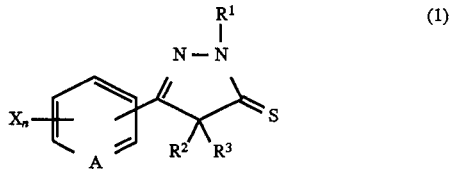

wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group which may have substituents, a phenylcarbonyl lower alkyl group, a lower alkylcarbonyl lower alkyl group, a group

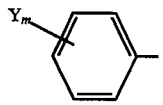

or a group

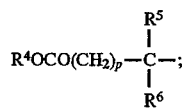

in which Y represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; m is 0 or an integer of 1 to 3; $R^4$ represents a lower alkyl group; p is 0, 1 or 2; $R^5$ and $R^6$ are the same or different and represent a hydrogen atom or a lower alkyl group; $R^2$ and $R^3$ are the same or different and represent a lower alkyl group or a cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, a cyano group, an amino group or a nitro group; n is 0 or an integer of 1 to 3; A represents ─(C)─ or ─(N)─ ; the substituent contained in the abovementioned benzyl group, phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

The groups represented by $R^1$, $R^2$, $R^3$ and X are explained in more detail below.

As a straight- or branched-chain alkyl group having 1 to 12 carbon atoms, a straight- or branched-chain alkyl group having 1 to 6 carbon atoms such as methyl, ethyl, n-propyl, isopropyl, n-butyl, sec-butyl, tert-butyl, n-pentyl, n-hexyl or the like, and besides, n-heptyl, n-octyl, n-nonyl, n-decyl, n-undecyl, n-dodecyl and the like are mentioned.

As a cycloalkyl group having 3 to 8 carbon atoms, cyclopropyl, cyclobutyl, cyclopentyl, cyclohexyl, cycloheptyl, cyclooctyl and the like are mentioned.

As a lower alkenyl group, a straight- or branched-chain alkenyl group having 2 to 6 carbon atoms such as vinyl, 1-propenyl, isopropenyl, allyl, 2-butenyl, 3-butenyl, 1-methylallyl, 2-methyl-2-butenyl, 2-pentenyl, 3-pentenyl, 2-hexenyl, 4-hexenyl and the like are mentioned.

As a lower alkynyl group, a straight- or branched-chain alkynyl group having 2 to 6 carbon atoms such as ethynyl, 2-propynyl, 2-butynyl, 3-butynyl, 1-methyl-2-propynyl, 2-pentynyl, 2-hexynyl and the like are mentioned.

As a lower alkoxycarbonyl group, a straight- or branched-chain alkoxycarbonyl group having 2 to 7 carbon atoms such as methoxycarbonyl, ethoxycarbonyl, n-propoxy, isopropoxycarbonyl, n-butoxycarbonyl, sec-butoxycarbonyl, tert-butoxycarbonyl, n-pentyloxycarbonyl, n-hexyloxycarbonyl and the like are mentioned.

As a phenylcarbonyl lower alkyl group, a straight- or branched-chain alkyl group containing 1 to 6 carbon atoms and having as substituents a phenylcarbonyl group, such as phenylcarbonylmethyl, 1-phenylcarbonylethyl, 2-phenylcarbonylethyl, 2-methyl-2-phenylcarbonylethyl, 3-phenylcarbonylpropyl, 4-phenylcarbonylbutyl, 5-phenylcarbonylpentyl, 6-phenylcarbonylhexyl and the like are mentioned.

As a lower alkylcarbonyl lower alkyl group, a straight- or branched-chain alkyl group containing 1 to 6 carbon atoms and having as substituents a straight- or branched-chain alkylcarbonyl group having 2 to 7 carbon atoms, such as methylcarbonylmethyl, 1-ethylcarbonylethyl, 2-methylcarbonylethyl, 2-methyl-2-methylcarbonylethyl, 3-methylcarbonylpropyl, 4-(n-propylcarbonyl)butyl, 5-methylcarbonylpentyl, 6-(t-butylcarbonyl)hexyl and the like are mentioned.

As a lower alkyl group, a straight- or branched-chain alkyl group having 1 to 6 carbon atoms such as methyl, ethyl, n-propyl, isopropyl, n-butyl, sec-butyl, tert-butyl, n-pentyl, n-hexyl and the like are mentioned.

As a halogen atom, fluorine, chlorine, bromine, iodine or the like are mentioned.

As a lower alkoxy group, a straight- or branched-chain alkoxy group having 1 to 6 carbon atoms such as methoxy, ethoxy, n-propoxy, isopropoxy, n-butoxy, sec-butoxy, tert-butoxy, n-pentyloxy, n-hexyloxy and the like are mentioned.

As a lower haloalkyl group, a straight- or branched-chain alkyl group having 1 to 6 carbon atoms and containing 1 to 3 halogen atoms, such as chloromethyl, bromomethyl, fluoromethyl, iodomethyl, dichloromethyl, trichloromethyl, difluoromethyl, trifluoromethyl, 1-chloroethyl, 2-chloroethyl, 2-fluoroethyl, 1, 2-dichloroethyl, 3-chloropropyl, 3-chloro-2-methylpropyl, 2, 3-dibromopropyl, 4-chlorobutyl, 5-chloropentyl, 6-chlorohexyl and the like are mentioned.

As a lower haloalkoxy group, a straight- or branched-chain alkoxy group having 1 to 6 carbon atoms and containing 1 to 3 halogen atoms, such as chloromethoxy, bromomethoxy, fluoromethoxy, iodomethoxy, dichloromethoxy, trichloromethoxy, difluoromethoxy, trifluoromethoxy, 1-chloroethoxy, 2-chloroethoxy, 2-fluoroethoxy, 1, 2-dichloroethoxy, 3-chloropropoxy, 3-chloro-2-methylpropoxy, 2, 3-dibromopropoxy, 4-chlorobutoxy, 5-chloropentyloxy, 6-chlorohexyloxy and the like are mentioned.

Benzyl groups which may have substituents are the benzyl groups having on the phenyl ring 1 to 3 substituents selected from the group consisting of a halogen atom, a lower alkyl group, a lower alkoxy group, a lower haloalkyl group, a nitro group, a cyano group and a lower alkoxycarbonyl. Specific examples of benzyl groups which may have on the phenyl ring as substituents 1 to 3 substituents selected from the group consisting of a halogen atom, a straight- or branched-chain alkyl group having 1 to 6 carbon atoms, a straight- or branched-chain alkoxy group having 1 to 6 carbon atoms, a straight- or branched-chain alkyl group having 1 to 6 carbon atoms and containing 1 to 3 halogen atoms as substituents, a nitro group, a cyano group, and a straight- or branched-chain alkoxycarbonyl group having 1 to 6 carbon atoms include benzyl, 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 3, 4-dichlorobenzyl, 3, 4, 5-trichlorobenzyl, 3, 4-dibromobenzyl, 3, 4, 5-tribromobenzyl, 2-methylbenzyl, 3-methylbenzyl, 4-methylbenzyl, 2-ethylbenzyl, 3-propylbenzyl, 4-butylbenzyl, 2-pentylbenzyl, 3-hexylbenzyl, 3, 4-dimethylbenzyl, 3, 4, 5-trimethylbenzyl, 2-methoxybenzyl, 3-methoxybenzyl, 4-methoxybenzyl, 2-ethoxybenzyl, 3-propoxybenzyl, 4-butoxybenzyl, 2-pentyloxybenzyl, 3-hexyloxybenzyl, 2, 4-dimethoxybenzyl, 3, 4-diethoxybenzyl, 3, 4, 5-trimethoxybenzyl, 2-trifluoromethylbenzyl, 3-(2-chloroethyl)benzyl, 2-(3-bromopropyl)benzyl, 4-iodomethylbenzyl, 2-(2, 3-dichloropropyl)benzyl, 3-(4-fluorobutyl)benzyl, 4-(3-chloro-2-methylpropyl)benzyl, 2-(5-bromohexyl)benzyl, 3-(5, 6-dichlorohexyl)benzyl, 4-(2, 2, 2-trichloroethyl)benzyl, 2-nitrobenzyl, 3-nitrobenzyl, 4-nitrobenzyl, 2, 3-dinitrobenzyl, 2, 4, 6-trinitrobenzyl, 2-cyanobenzyl, 3-cyanobenzyl, 4-cyanobenzyl, 2-methoxycarbonylbenzyl, 3-methoxycarbonylbenzyl, 4-methoxycarbonylbenzyl, 2-ethoxycarbonylbenzyl, 3-ethoxycarbonylbenzyl, 4-ethoxycarbonylbenzyl and the like.

Phenoxy groups which may have substituents are the phenoxy groups having on the phenyl ring 1 to 3 substituents selected from the group consisting of a halogen atom, a lower alkyl group, a lower alkoxy group, a lower haloalkyl group, a nitro group, a cyano group and a lower alkoxycarbonyl group. Specific examples of phenoxy groups which may have on the phenyl ring 1 to 3 groups selected from the group consisting of a halogen atom, a straight- or branched-chain alkyl group having 1 to 6 carbon atoms, a straight- or branched-chain alkoxy group having 1 to 6 carbon atoms, a straight- or branched-chain alkyl group having 1 to 6 carbon atoms and containing 1 to 3 halogen atoms, a nitro group, a cyano group, and a straight- or branched-chain alkoxycarbonyl group having 1 to 6 carbon atoms include phenoxy, 2-chlorophenoxy, 3-chlorophenoxy, 4-chlorophenoxy, 2-bromophenoxy, 3-bromophenoxy, 4-bromophenoxy, 2-fluorophenoxy, 3-fluorophenoxy, 4-fluorophenoxy, 3, 4-dichlorophenoxy, 3, 4, 5-trichloromethoxy, 3, 4-dibromophenoxy, 3, 4, 5-tribromophenoxy, 2-methylphenoxy, 3-methylphenoxy, 4-methylphenoxy, 2-ethylphenoxy, 3-propylphenoxy, 4-butylphenoxy, 2-pentylphenoxy, 3-hexylphenoxy, 3, 4-dimethylphenoxy, 3, 4, 5-trimethylphenoxy, 2-methoxyphenoxy, 3-methoxyphenoxy, 4-methoxyphenoxy, 2-ethoxyphenoxy, 3-propoxyphenoxy, 4-butoxyphenoxy, 2-pentyloxyphenoxy, 3-hexyloxyphenoxy, 2, 4-dimethoxyphenoxy, 3, 4-diethoxyphenoxy, 3, 4, 5-trimethoxyphenoxy, 2-trifluoromethylphenoxy, 3-(2-chloroethyl)phenoxy, 2-(3-bromopropyl)phenoxy, 4-iodomethylphenoxy, 2-(2, 3-dichloropropyl)phenoxY, 3-(4-fluorobutyl)phenoxy, 4-(3-chloro-2-methylpropyl)phenoxy, 2-(5-bromohexyl)phenoxy, 3-(5, 6-dichlorohexyl)phenoxy, 4-(2, 2, 2-trichloroethyl)phenoxy, 2-nitrophenoxy, 3-nitrophenoxy, 4-nitrophenoxy, 2, 3-dinitrophenoxy, 2, 4, 6-trinitrophenoxy, 2-cyanophenoxy, 3-cyanophenoxy, 4-cyanophenoxy, 2-methoxycarbonylphenoxy, 3-methoxycarbonylphenoxy, 4-methoxycarbonylphenoxy, 2-ethoxycarbonylphenoxy, 3-ethoxycarbonylphenoxy, 4-ethoxycarbonylphenoxy and the like.

Phenyl groups which may have substituents are the phenyl groups having 1 to 3 substituents selected from the group consisting of a halogen atom, a lower alkyl group, a lower alkoxy group, a lower haloalkyl group, a nitro group, a cyano group and a lower alkoxycarbonyl group. Specific examples of phenyl groups which may have on the phenyl ring 1 to 3 groups selected from the group consisting of a halogen atom, a straight- or branched-chain alkyl group having 1 to 6 carbon atoms, a straight- or branched-chain alkoxy group having 1 to 6 carbon atoms, a straight- or branched-chain alkyl group having 1 to 6 carbon atoms and containing 1 to 3 halogen atoms, a nitro group, a cyano group, and a straight- or branched-chain alkoxycarbonyl group having 1 to 6 carbon atoms include phenyl, 2-chlorophenyl, 3-chlorophenyl, 4-chlorophenyl, 2-bromophenyl, 3-bromophenyl, 4-bromophenyl, 2-fluorophenyl, 3-fluorophenyl, 4-fluorophenyl, 3, 4-dichlorophenyl, 3, 4, 5-trichlorophenyl, 3, 4-dibromophenyl, 3, 4, 5-tribromophenyl, 2-methylphenyl, 3-methylphenyl, 4-methylphenyl, 2-ethylphenyl, 3-propylphenyl, 4-butylphenyl, 2-pentylphenyl, 3-hexylphenyl, 3, 4-dimethylphenyl, 3, 4, 5-trimethylphenyl, 2-methoxyphenyl, 3-methoxyphenyl, 4-methoxyphenyl, 2-ethoxyphenyl, 3-propoxyphenyl, 4-butoxyphenyl, 2-pentyloxyphenyl, 3-hexyloxyphenyl, 2, 4-dimethoxyphenyl, 3, 4-diethoxyphenyl, 3, 4, 5-trimethoxyphenyl, 2-trifluoromethylphenyl, 3-(2-chloroethyl)phenyl, 2-(3-bromopropyl)phenyl, 4-iodomethylphenyl, 2-(2, 3-dichloropropyl)phenyl, 3-(4-fluorobutyl)phenyl, 4-(3-chloro-2-methylpropyl)phenyl, 2-(5-bromohexyl)phenyl, 3-(5, 6-dichlorohexyl)phenyl, 4-(2, 2, 2-trichloro-ethyl)phenyl, 2-nitrophenyl, 3-nitrophenyl, 4-nitrophenyl, 2, 3-dinitrophenyl, 2, 4, 6-trinitrophenyl, 2-cyanophenyl, 3-cyanophenyl, 4-cyanophenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl and the like.

4, 5-dihydropyrazole-5-thione derivatives represented by the above general formula (1) include a 4, 5-dihydropyrazole-5-thione derivative represented by the following general formula (1a), a 4, 5-dihydropyrazole-5-thione derivative represented by the following general formula (1b), and a 4, 5-dihydropyrazole-5-thione derivative represented by the following general formula (1c).

A 4, 5-dihydropyrazole-5-thione derivative represented by the general formula

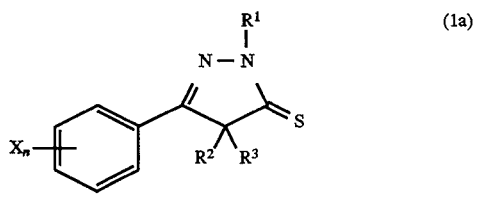

(1a)

wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group which may have substituents, a phenylcarbonyl lower alkyl group or a lower alkylcarbonyl lower alkyl group; $R^2$ $R^3$ and are the same or different and represent a lower alkyl group or a cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a phenoxy group which may have substituents, a phenyl group which may have substituents, a cyano group or a nitro group; n is 0 or an integer of 1 to 3; and the substituent contained in the abovementioned benzyl group, phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

A 4, 5-dihydropyrazole-5-thione derivative represented by the general formula

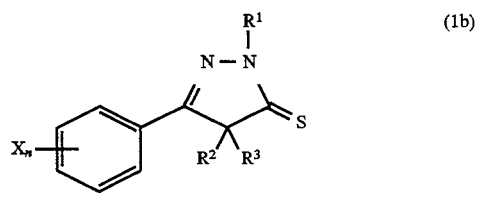

(1b)

wherein $R^1$ represents a group

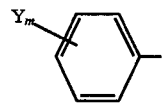

or a group

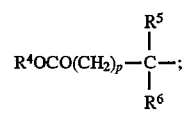

in which Y represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; m is 0 or an integer of 1 to 3; $R^4$ represents a lower alkyl group; p is 0, 1 or 2; $R^5$ and $R^6$ are the same or different and represent a hydrogen atom or a lower alkyl group; $R^2$ and $R^3$ are the same or different and represent a lower alkyl group or a lower cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; n is 0 or an integer of 1 to 3; and the substituent contained in the above-mentioned phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

A 4, 5-dihydropyrazole-5-thione derivative represented by the general formula

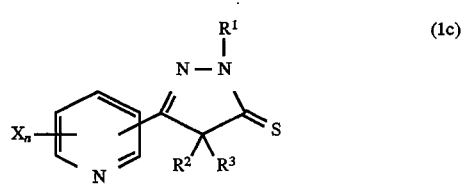

(1c)

wherein $R^1$ represents a phenyl group which may have substituents selected from the group consisting of a halogen atom, a lower alkyl group, a lower alkoxy group, a lower haloalkyl group and a nitro group, or a lower alkyl group; $R^2$ and $R^3$ each represent a lower alkyl group; and X represents a hydrogen atom, a halogen atom, a lower alkyl group, a lower alkoxy group, a lower haloalkyl group, an amino group or a nitro group.

Preferred compounds as the 4, 5-dihydropyrazole-5-thione derivative represented by the general formula (1a) are listed below.

A 4, 5-dihydropyrazole-5-thione derivative represented by the general formula (1a) wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group, a phenylcarbonyl lower alkyl group or a lower alkylcarbonyl lower alkyl group; $R^2$ and $R^3$ are both lower alkyl group; X represents a halogen atom, a lower alkyl group, a lower alkoxy group, a lower haloalkyl group, a cyano group or a nitro group; and n is 0, 1 to 2.

A 4, 5-dihydropyrazole-5-thione derivative represented by the general formula (Ia) wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group, a phenylcarbonyl lower alkyl group or a lower alkylcarbonyl lower alkyl group; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a cycloalkyl group having 3 to 8 carbon atoms; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a lower alkenyl group; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a lower alkynyl group; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a benzyl group; $R^2$ and $R^3$ are both lower alkyl group; X represents a halogen atom; and n is 0, 1 or 2.

A 4, 5-dihydropyrazole-5-thione derivative represented by the general formula (Ia) wherein $R^1$ represents a phenylcarbonyl lower alkyl group; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a lower alkylcarbonyl lower alkyl group; $R^2$ and $R^3$ are both lower alkyl group; X represents a halogen atom; and n is 0 or 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a halogen atom, a lower alkyl group, a lower alkoxy group, a lower haloalkyl group, a cyano group or a nitro group; and n is 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a halogen atom; and n represents 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a lower alkyl group; and n is 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a lower alkoxy group; and n is 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a lower haloalkyl group; and n is 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a cyano group; and n is 1.

A 4, 5-dihydropyrazole-5-thione derivative represented by the general formula (Ia) wherein $R^1$ represents a straight- or branched-chain alkyl group having 1 to 12 carbon atoms; $R^2$ and $R^3$ are both lower alkyl group; X represents a nitro group; and n is 1.

4, 5-dihydropyrazole-5-thione derivatives represented by the general formula (Ib) are divided into two groups; one is the compound represented by the general formula (Ib-1) wherein $R^1$ represents a group

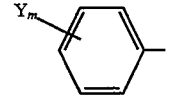

and the other is the compound represented by the general formula (Ib-2) wherein $R^1$ represents a group

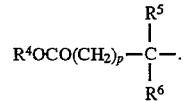

Preferred compounds as the 4, 5-dihydropyrazole-5-thione derivative of the general formula (Ib-1) are listed below.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group or $R^2$ and $R^3$ may be combined to form a cycloalkyl ring having 3 to 8 carbon atoms; X represents a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X represents a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-1) wherein Y represents a halogen atom; m is 0 or 1; $R^2$ and $R^3$ are both lower alkyl group; X represents a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-1) wherein Y represents a lower alkyl group; m is 0 or 1; $R^2$ and $R^3$ are both lower alkyl group; X represents a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-1) wherein Y represents a lower alkoxy group; m is 0 or 1; $R^2$ and $R^3$ are both lower alkyl group; X represents a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X represents a halogen atom; and n is 0, 1 or 2.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X represents a lower alkyl group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X is a lower alkoxy group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X is a lower haloalkyl group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X is a lower alkoxycarbonyl group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X is a phenyl group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are both lower alkyl group; X is a nitro group; and n is 0 or 1.

A 4, 5-dihydropyrazole-5-thione derivative of the general formula (Ib-1) wherein Y represents a halogen atom, a lower alkyl group or a lower alkoxy group; m is 0 or 1; $R^2$ and $R^3$ are combined to form a cycloalkyl ring having 3 to 8 carbon atoms; X is a halogen atom; and n is 0, 1 or 2.

Preferred compounds as the 4, 5-dihydropyrazole-5-thione derivative of the general formula (Ib-2) are listed below.

A 4, 5-dihydropyrazole-5-thione derivative of the general formula (Ib-2) wherein $R^4$ is a lower alkyl group; p is 0, 1 or 2; $R^5$ and $R^6$ are the same or different and represent a hydrogen atom or a lower alkyl group; $R^2$ and $R^3$ are both lower alkyl group; X is a halogen atom, a lower alkyl group, a lower alkoxy group, a lower haloalkyl group, a lower alkoxycarbonyl group, a phenyl group or a nitro group; and n is 0, 1 or 2.

A 4, 5-dihydropyrazole-5-thione derivative of the general formula (Ib-2) wherein $R^4$ is a lower alkyl group; p is 0, 1 or 2; $R^5$ and $R^6$ are the same or different and represent a hydrogen atom or a lower alkyl group; $R^2$ and $R^3$ are both lower alkyl group; X is a halogen atom; and n is 0 or 1.

A 4, 5-dihydropyrazole-5-thione derivative of the general formula (Ib-2) wherein $R^4$ is a lower alkyl group; p is 0, 1 or 2; $R^5$ and $R^6$ are the same or different and represent a hydrogen atom or a methyl group; $R^2$ and $R^3$ are both lower alkyl group; X is a halogen atom; and n is 0 or 1.

Preferred compounds as the 4, 5-dihydropyrazole-5-thione derivative represented by the general formula (Ic) are listed below.

A 4, 5-dihydropyrazole-5-thione derivative represented by the general formula (Ic) wherein $R^1$ represents a lower alkyl group.

A 4, 5-dihydropyrazole-5-thione derivative represented by the general formula (Ic) wherein $R^1$ is a phenyl group which may have substituents selected from the group consisting of a halogen atom, a lower alkyl group, a lower alkoxy group, a lower haloalkyl group and a nitro group.

The compound of the present invention is prepared by the process illustrated below in Reaction Scheme 1.

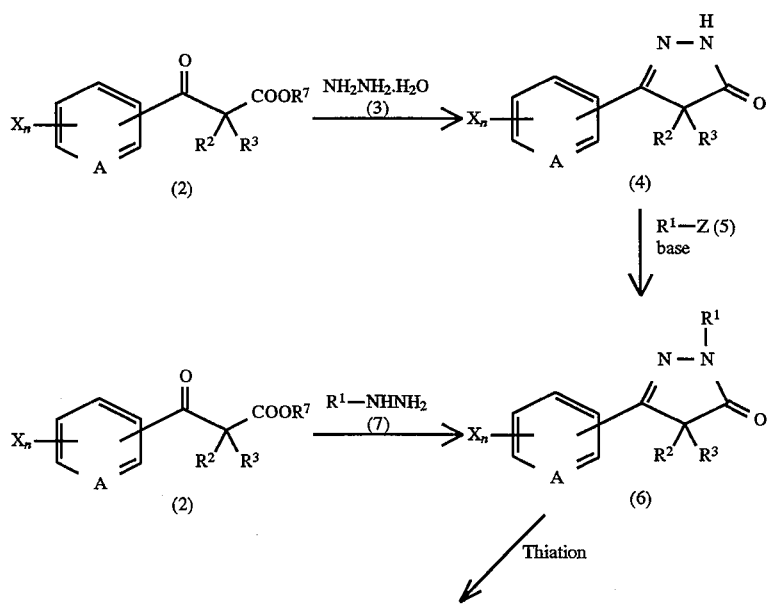

Reaction Scheme 1

-continued
Reaction Scheme 1

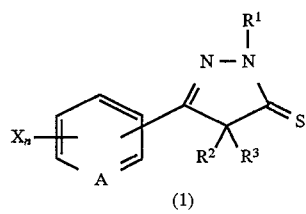

(1)

wherein $R^1$, $R^2$, $R^3$ and X are as defined above; $R^7$ represents a lower alkyl group; and Z represents a removable group such as a halogen atom or the like.

In accordance with Reaction Scheme 1 illustrated above, a 4, 5-dihydropyrazole-5-thione derivative represented by the general formula (1) is prepared by the following process : the acetate represented by the general formula (2) is reacted with hydrazine hydrate of the general formula (3) to afford a dihydropyrazolone of the general formula (4), the produced dihydropyrazolone of the general formula (4) is reacted with the alkylating agent of the formula (5) to give a 4, 5-dihydropyrazol-5-one derivative represented by the general formula (6), and then the thus produced 4, 5-dihydropyrazol-5-one derivative represented by the general formula (6) is thiated. Alternatively, a 4, 5-dihydropyrazole-5-thione derivative represented by the general formula (1) is prepared by reacting the acetate represented by the general formula (2) with the hydrazine of the general formula (7) to afford a 4, 5-dihydropyrazol-5-one derivative of the general formula (6), and then the produced 4, 5-dihydropyrazol-5-one derivative of the general formula (6) is thiated.

Reaction between the acetate of the general formula (2) and hydrazine hydrate of the general formula (3) may be carried out in a suitable solvent. Examples of solvents employed in the reaction include, for example, alcohols such as methanol, ethanol, etc., aromatic hydrocarbons such as benzene, toluene, etc., and organic acids such as acetic acid, propionic acid, etc. The proportions of the acetate of the general formula (2) and hydrazine hydrate of the general formula (3) are not specifically limited, but usually about 0.5 to about 2 moles, preferably about 1 to about 1.2 moles, of the latter is used per mole of the former. The above reaction proceeds well at a temperature ranging from 10° C. to the boiling point of the solvent used, and is generally completed in about 1 to about 24 hours.

In the reaction described above, the compound (2) used as a starting material is a readily available industrial compound or it can easily be produced according to the conventional method. The compound can be readily produced by the Reformatsky reaction between the corresponding benzoates and the corresponding bromoacetates, as described, for example, in Journal of Organic Chemistry, Vol. 56, pp. 2587 (1991). The compound can also be readily produced by the Claisen condensation reaction between the corresponding pyridinecarboxylates and the corresponding substituted acetates. Hydrazine hydrate of the formula (3) used as another starting material is a readily available industrial compound.

The reaction for preparing a 4, 5-dihydropyrazol-5-one derivative of the general formula (6) from the dihydropyrazolone of the general formula (4) is performed by reacting in the presence of a suitable base the dihydropyrazolone of the general formula (4) with the corresponding alkylating agent of the general formula (5) such as alkyl halide and so on in an appropriate solvent. Examples of solvents used in the reaction are nitriles such as acetonitrile, propionitrile, etc., ketones such as acetone, methyl ethyl ketone, etc., alcohols such as methanol, ethanol, etc., amides such as dimethylformamide, dimethylacetamide, etc. and mixtures thereof. Examples of bases used in the reaction are carbonates of alkaline metal such as sodium carbonate, potassium carbonate, etc., hydroxides of alkaline metal such as sodium hydroxide, potassium hydroxide, etc., hydrides of alkaline metal such as sodium hydride, potassium hydride, etc., metal alkoxides such as sodium methoxide, sodium ethoxide, etc., tertiary amines such as triethylamine, pyridine, etc. As to the amount of bases employed in the reaction, about 1 to about 3 moles, preferably about 1 to about 1.5 moles, of the base is used per mole of dihydropyrazolone of the general formula (4). As to the proportion of dihydropyrazolone of the general formula (4) and the alkylating agent of the general formula (5), about 0.5 to about 2 moles, preferably about 1 to about 1.2 moles, of the latter is used per mole of the former. The above reaction proceeds well at a temperature ranging from 0° C. to the boiling point of the solvent used, and is generally completed in about 1 to about 24 hours. The alkylating agent of the formula (5) used in the reaction is commercially available or it can be readily produced according to the conventional method.

Reaction between the acetate of the general formula (2) and the hydrazine of the general formula (7) is carried out under similar conditions to those of the reaction between the acetate of the general formula (2) and hydrazine hydrate of the general formula (3). Hydrazines of the general formula (7) used in the reaction are readily available industrial compounds.

Thiation of 4, 5-dihydropyrazol-5-one derivative of the general formula (6) to produce the compound represented by the general formula (1) can be performed usually in a suitable solvent. Examples of solvents usable in the reaction include, for example, aromatic hydrocarbons such as benzene, toluene, etc., carbon disulfide, and mixtures thereof. Examples of thiating agents include diphosphorus pentasulfide, Lawesson's reagent (2, 4-bis(4-methoxyphenyl)-1, 3-dithia-2, 4-diphosphetane-2, 4-disulfide), etc. As to the proportions of 4, 5-dihydropyrazol-5-one derivative of the general formula (6) and the thiating agent, about 0.5 to about 5 moles, preferably from about 0.5 to about 1.5 moles, of the latter is used per mole of the former. The above reaction progresses at a temperature ranging from room temperature to the boiling point of the solvent used, and is generally completed in about 1 to about 24 hours.

Among the compounds of the present invention, the compound of the general formula (1b-1) is readily prepared by the process illustrated below in Reaction Scheme 2.

Reaction Scheme 2

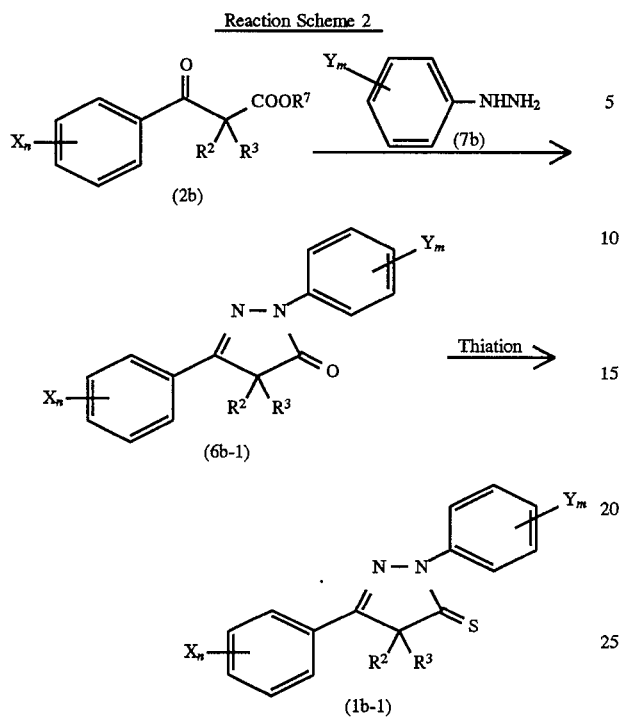

wherein $R^2$, $R^3$, $R^7$, X, Y, n and m are as defined above.

In accordance with Reaction Scheme 2, the compound represented by the general formula (1b-1) is prepared by the following process: the benzoylacetate represented by the general formula (2b) is reacted with the hydrazine represented by the general formula (7b) and the produced 4,5-dihydropyrazol-5-one derivative of the general formula (6b-1) is thiated.

Reaction between the benzoylacetate of the general formula (2b) and the hydrazine of the general formula (7b) is carried out under similar reaction conditions to those of the reaction between the acetate of the general formula (2) and the hydrazine of the general formula (7) performed in Reaction Scheme 1.

Thiation of 4, 5-dihydropyrazol-5-one derivative of the general formula (6b-1) is effected under similar reaction conditions to those of the thiation of 4, 5-dihydropyrazol-5-one derivative of the general formula (6) performed in Reaction Scheme 1.

Among the compounds of the present invention, the compound of the general formula (1b-2) is readily prepared, for example, by the process illustrated below in Reaction Scheme 3.

Reaction Scheme 3

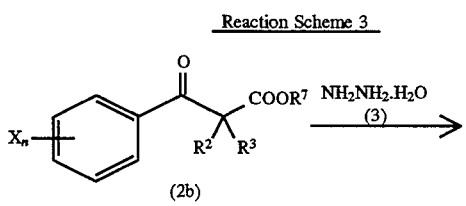

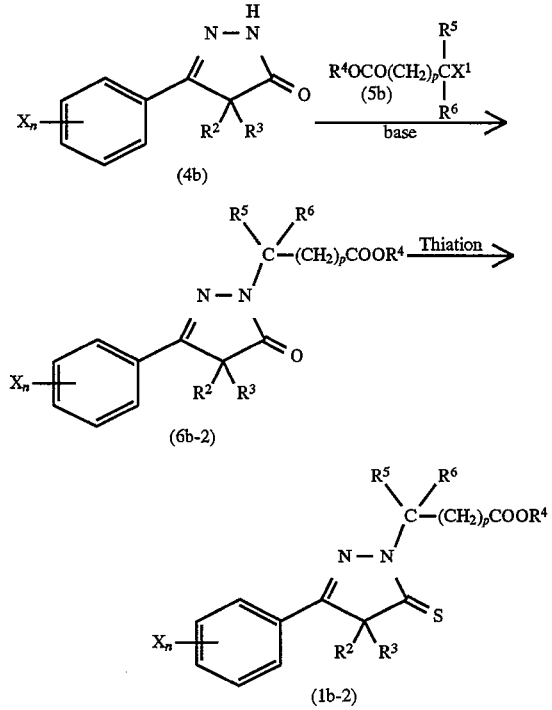

wherein $R^2$, $R^3$, $R^4$, $R^5$, $R^6$, $R^7$, X, n and p are as defined above; and X represents a halogen atom.

In accordance with Reaction Scheme 3, the compound represented by the general formula (1b-2) is prepared by the following process: the benzoylacetate represented by the general formula (2b) is reacted with hydrazine hydrate of the general formula (3) and the produced dihydropyrazolone represented by the general formula (4b) is reacted with the alkylating agent of the general formula (5b), and then the resultant compound of the general formula (6b-2) is thiated.

Reaction between the benzoylacetate of the general formula (2b) and hydrazine hydrate of the general formula (3) is carried out under similar reaction conditions to those of the reaction between the acetate of the general formula (2) and hydrazine hydrate of the general formula (3).

Reaction between the dihydropyrazolone of the general formula (4b) and the alkylating agent of the general formula (5b) is carried out under similar reaction conditions to those of the reaction between the dihydropyrazolone of the general formula (4) and the alkylating agent of the formula (5) performed in Reaction Scheme 1.

Thiation of the compound represented by the general formula (6b-2) is effected under similar reaction conditions to those of the thiation of 4, 5-dihydropyrazol-5-one derivative of the general formula (6) performed in Reaction Scheme 1.

The compound of the present invention prepared by the above processes is readily isolated and purified from the reaction mixture by means of conventional separating methods such as solvent extraction, recrystallization, column chromatography, etc. Therefore, in accordance with the above-mentioned methods, the compounds of the present invention can be prepared in high yield and in high purity.

The compound of the present invention acts effectively against a broad range of spider mites belonging to Tetranychus genus and Panonychus genus, and the spider mites to which the compounds of the present invention are effectively applied include *Tetranychus urticae* Koch, *Tetranychus kanzawai* Kishida, *Panonychus citri* McGregor, *Panonychus ulmi* Koch, etc.

For use as a miticide, the compound of the present invention is made available in the form of emulsions, wettable powders, water soluble chemicals, particles, microparticles, granules, powders, coating compositions, spray preparations, aerosols, microcapsules, fumigants, smoking agents, etc. In preparing these forms, various surfactants may be used to effect emulsification, dispersal, suspension, or foaming. Examples of surfactants include nonionic surfactants such as polyoxyethylenealkylether, polyoxyethylenealkylester, polyoxyethylenesorbitanalkylester, etc., and anionic surfactants such as alkylbenzenesulphonate, alkylsulphosuccinate, alkylsulfate, polyoxyethylenealkylsulfate, allylsulfonate, lignin sulfite, etc.

Usable as solubilizers, diluents and carriers are a variety of organic solvents, aerosol spraying agents, natural minerals and synthetic compounds or the like. As organic solvents, benzene, toluene, xylene, ethylbenzene, chlorobenzene, alkylnaphthalene, chloroethylene, cyclohexane, methyl ethyl ketone, methyl isobutyl ketone, alcohols, cellosolves, dimethylformamide, dimethyl sulfoxide, acetonitrile, mineral oil fractions, water and so on are preferably employed. As aerosol spraying agents, propane, butane, hydrocarbon halide, nitrogen, carbon dioxide and the like are usable. Such forms can be colored with an organic or inorganic dye.

The compound of the present invention is usually included to give the concentration from about 0.1 to 95 weight %, preferably from about 0.5 to 90 weight %. The above forms prepared are used as such or as diluted with a carrier or water. In conformity with the contemplated purpose, the composition as an active ingredient is employed as diluted to provide a concentration from 0.0001 to 100 weight %, preferably from 0.001 to 10 weight %.

Best Mode of Carrying Out the Invention

Given below are Reference Examples for preparing intermediates for the compounds according to the present invention, Examples for producing the compounds according to the present invention, and Test Examples to further illustrate the present invention.

Reference Example 1

Preparation of 3-(4-chlorophenyl)-4, 5-dihydropyrazol-5-one

A mixture of 26 g (0.10 mol) of ethyl $\alpha$-(4-chlorobenzoyl)isobutyrate, 10 g (0.20 mol) of hydrazine monohydrate and 200 ml of ethanol was heated under reflux for 18 hours. The reaction solution was concentrated under reduced pressure. The obtained crude product was washed successively with water, methanol-water and diethyl ether-n-hexane and then air dried, to give 16 g of the object compound as white crystals (yield 84%).

Melting point : 145°–146° C. $^1$H-NMR (CDCl$_3$) $\delta$ ppm: 1.51 (s, 6H), 7.57 (dd, 4H), 9.0 (brs, 9H)

Reference Example 2

Preparation of 3-(4-chlorophenyl)-1-propyl-4, 5-dihydropyrazol-5-one

To a suspension of 0.22 g (5.5 mmol) of 60% oily sodium hydride in 10 ml of anhydrous dimethylformamide was added dropwise a solution of 1.0 g (4.5 mmol) of 3-(4-chlorophenyl)-4, 5-dihydropyrazol-5-one in dimethylformamide (5 ml) at 0° C. After 30 minutes of stirring at room temperature, 0.83 g (6.7 mmol) of 1-bromopropane was added dropwise and stirring was continued for another 2 hours. To the reaction solution was added 50 ml of diethyl ether and 50 ml of water, and vigorously agitated. The resulting solution was separated, and the aqueous layer was extracted twice with 50 ml of diethyl ether. The organic layer was combined and washed successively with water and saturated brine solution, and dried over anhydrous sodium sulfate. Then the solvent was evaporated under reduced pressure. The obtained crude product was purified by silica gel column chromatography (n-hexane/ethyl acetate=4/1 (v/v)) to give 1.1 g of the object compound as a colorless oil (yield 92%).

$^1$H-NMR (CDCl$_3$) $\delta$ ppm: 0.96 (t, 3H), 1.48 (s, 6H), 1.3–2.2 (m, 3H), 3.72 (s, 6H), 7.57 (dd, 4H)

Reference Example 3

Preparation of 3-(4-chlorophenyl)-1-t-butyl-4, 5-dihydropyrazol-5-one

After 1.5 g (12 mmol) of t-butylhydrazine hydrochloride was stirred in 30 ml of acetic acid which contains 0.97 g (12 mmol) of sodium acetate for 30 minutes, 2.0 g (7.9 mmol) of ethyl $\alpha$-(4-chloro-benzoyl)isobutyrate was added thereto, and the mixture was heated under reflux for 20 hours. Acetic acid was evaporated under reduced pressure, and to the obtained residue was added 50 ml of diethyl ether and 50 ml of water, and then vigorously agitated. The resulting solution was separated, and the aqueous layer was extracted twice with 50 ml of diethyl ether. The organic layer was combined and washed successively with water, 1N hydrochloric acid and saturated brine solution, and dried over anhydrous sodium sulfate. Then the solvent was evaporated under reduced pressure. The obtained crude product was purified by silica gel column chromatography (n-hexane/ethyl acetate=5/1 (v/v)) to give 1.4 g of the object compound as white crystals (yield 68%).

Melting point : 73°–75° C. $^1$H-NMR (CDCl$_3$) $\delta$ ppm: 1.40 (s, 6H), 1.55 (s, 9H), 7.53 (dd, 4H)

Reference Example 4

Preparation of 3-(4-chlorophenyl)-1-(3, 3-dimethyl-2-oxobutyl)-4, 5-dihydropyrazol-5-one A mixture of 3.5 g (16 mmol) of 3-(4-chlorophenyl)-4, 5-dihydropyrazol-5-one, 2.9 g (24 mmol) of chloropinacolone, 5.4 g (39 mmol) of anhydrous potassium carbonate and acetonitrile was heated under reflux for 14 hours. Excess potassium carbonate and the formed salts were removed by filtration. The filtrate was concentrated and the residue was purified by silica gel column chromatography (n-hexane/ethyl acetate=4/1 (v/v)) to give 4.9 g of the object compound as white crystals (yield 97%).

Melting point : 84°–86° C. $^1$H-NMR (CDCl$_3$) $\delta$ ppm: 1.23 (s, 9H), 1.50 (s, 6H), 4.69 (s, 2H), 7.48 (dd, 4H)

Example 1

Preparation of 3-(4-chlorophenyl)-1-propyl-4, 5-dihydropyrazole-5-thione (Compound No. 1)

A mixture of 1.0 g (3.8 mmol) of 3-(4-chlorophenyl)-1-propyl-4, 5-dihydropyrazol-5-one, 1.2 g (3.0 mmol) of Lawesson's reagent, and 10 ml of toluene was heated under reflux for 2 hours. The reaction solution was concentrated and the residue was purified by silica gel column chromatography (n-hexane/ethyl acetate=10/1 (v/v)) to give 1.0 g of the object compound as a yellow oil (yield 94%).

$^1$H-NMR (CDCl$_3$) $\delta$ ppm: 0.97 (t, 3H), 1.5–2.3 (m, 3H), 1.52 (s, 6H), 4.14 (s, 6H), 7.57 (dd, 4H)

Similarly to Example 1 described above, various compounds (Compound No. 2 to Compound No. 32) were obtained as shown in Table 1 below. Table 1 also shows the property of the compounds.

TABLE 1

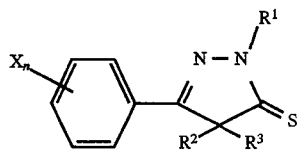

| Compound No. | Xn | R¹ | R² | R³ | Property |
|---|---|---|---|---|---|
| 1 | 4-chloro | n-propyl | methyl | methyl | yellow oil |
| 2 | hydrogen atom | methyl | methyl | methyl | mp: 117–118° C. |
| 3 | hydrogen atom | n-propyl | methyl | methyl | yellow oil |
| 4 | hydrogen atom | benzyl | methyl | methyl | mp: 95–97° C. |
| 5 | 3-chloro | methyl | methyl | methyl | mp: 60–61° C. |
| 6 | 4-chloro | methyl | methyl | methyl | mp: 94–95° C. |
| 7 | 4-chloro | n-propyl | methyl | iso-propyl | yellow oil |
| 8 | 4-chloro | isopropyl | methyl | methyl | yellow oil |
| 9 | 4-chloro | isobutyl | methyl | methyl | yellow oil |
| 10 | 4-chloro | t-butyl | methyl | methyl | yellow oil |
| 11 | 4-chloro | n-hexyl | methyl | methyl | yellow oil |
| 12 | 4-chloro | cyclohexyl | methyl | methyl | mp: 112–113° C. |
| 13 | 4-chloro | allyl | methyl | methyl | yellow oil |
| 14 | 4-chloro | propargyl | methyl | methyl | yellow oil |
| 15 | 4-chloro | benzyl | methyl | methyl | mp: 127–128° C. |
| 16 | 4-chloro | phenyl-carbonyl-methyl | methyl | methyl | mp: 111–113° C. |
| 17 | 4-chloro | t-butyl-carbonyl-methyl | methyl | methyl | mp: 107–108° C. |
| 18 | 4-fluoro | n-propyl | methyl | methyl | mp: 59–60° C. |
| 19 | 4-bromo | methyl | methyl | methyl | mp: 106–107° C. |
| 20 | 4-bromo | n-propyl | methyl | methyl | mp: 71–72° C. |
| 21 | 4-trifluoro-methyl | methyl | methyl | methyl | mp: 104–105° C. |
| 22 | 4-trifluoro-methyl | n-propyl | methyl | methyl | mp: 39–40° C. |
| 23 | 4-methyl | n-propyl | methyl | methyl | mp: 59–60° C. |
| 24 | 4-ethyl | n-propyl | methyl | methyl | yellow oil |
| 25 | 4-isopropyl | n-propyl | methyl | methyl | yellow oil |
| 26 | 4-t-butyl | n-propyl | methyl | methyl | mp: 67–68° C. |
| 27 | 4-methoxy | n-propyl | methyl | methyl | yellow oil |
| 28 | 4-methoxy | isobutyl | methyl | methyl | yellow oil |
| 29 | 4-methoxy | n-hexyl | methyl | methyl | yellow oil |
| 30 | 4-nitro | n-propyl | methyl | methyl | mp: 113–114° C. |
| 31 | 4-cyano | n-propyl | methyl | methyl | mp: 88–89° C. |
| 32 | 3,4-dichloro | benzyl | methyl | methyl | mp: 89–91° C. |

In the above Table 1, the compounds whose property is shown to be yellow oil have NMR spectra as indicated below.

$^1$H-NMR (CDCl$_3$) δ ppm;

Compound No. 3: 0.97 (t, 3H), 1.5–2.2 (m, 2H), 1.53 (s, 6H), 4.14 (t, 2H), 7.1–7.6 (m, 3H), 7.7–8.0 (m, 2H)

Compound No. 7: 0.80 (d, 3H), 0.95 (t, 3H), 1.00 (d, 3H), 1.55 (s, 3H), 1.5–2.6 (m, 3H), 7.55 (dd, 4H)

Compound No. 8: 1.41 (d, 6H), 1.52 (s, 6H), 5.0–5.5 (m, 1H), 7.64 (dd, 4H)

Compound No. 9: 0.97 (d, 6H), 1.3–2.1 (m, 3H), 1.52 (s, 6H), 4.19 (t, 2H), 7.60 (dd, 4H)

Compound No. 10: 1.47 (s, 6H), 1.76 (s, 9H), 7.53 (dd, 4H)

Compound No. 11: 0.6–2.2 (m, 11H), 1.54 (s, 6H), 4.19 (t, 2H), 7.62 (dd, 4H)

Compound No. 13: 1.53 (s, 6H), 4.7–4.9 (m, 2H), 5.0–5.5 (m, 2H), 5.6–6.4 (m, 1H), 7.58 (dd, 4H)

Compound No. 14: 1.54 (s, 6H), 2.2–2.5 (m, 1H), 4.9–5.1 (m, 2H), 7.61 (dd, 4H)

Compound No. 24: 0.95 (t, 3H), 1.25 (t, 3H), 1.55 (s, 6H), 1.5–2.1 (m, 2H), 2.65 (q, 2H), 4.15 (t, 2H), 7.45 (dd, 4H)

Compound No. 25: 0.95 (t, 3H), 1.25 (d, 6H), 1.50 (s, 6H), 1.5–2.1 (m, 2H), 2.6–3.2 (m, 1H), 4.10 (t, 2H), 7.45 (dd, 4H)

Compound No. 27: 0.95 (t, 3H), 1.50 (s, 6H), 1.5–2.1 (m, 2H), 3.80 (s, 3H), 4.10 (t, 2H), 7.30 (dd, 4H)

Compound No. 28: 0.98 (d, 6H), 1.3–2.1 (m, 3H), 1.52 (s, 6H), 3.81 (s, 3H), 4.17 (t, 2H), 7.46 (dd, 4H)

Compound No. 29: 0.6–2.1 (m, 11H), 1.55 (s, 6H), 3.83 (s, 3H), 4.18 (t, 2H), 7.40 (dd, 4H)

Reference Example 5

Preparation of 1-phenyl-3-(4-methylphenyl)-4, 5-dihydropyrazol-5-one

A mixture of 15 g (64 mmol) of ethyl α-(4-methylbenzoyl)isobutyrate, 10 g (93 mmol) of phenylhydrazine and 100 ml of toluene was dehydrated under reflux in the presence of p-toluenesulfonic acid monohydrate (catalytic amount) for 18 hours. The reaction solution was washed successively with 1N sodium hydroxide, 1N hydrochloric acid and saturated brine solution, and dried over anhydrous magnesium sulfate. Then the solvent was evaporated under reduced pressure. The obtained crude product was recrystallized from methanol to give 15 g of the object compound as white crystals (yield 84%).

Melting point: 112°–113° C. $^1$H-NMR (CDCl$_3$) δ ppm: 1.56 (s, 6H), 2.37 (s, 3H), 6.9–8.2 (m, 9H)

Reference Example 6

Preparation of 3-(4-chlorophenyl)-4, 5-dihydropyrazol-5-one

A mixture of 26 g (0.10 mmol) of ethyl α-(4-chlorobenzoyl)isobutyrate, 10 g (0.20 mmol) of hydrazine monohydrate and 200 ml of ethanol was heated under reflux for 18 hours. The reaction solution was concentrated under reduced pressure. The obtained crude product was washed successively with water, methanol-water and diethyl ether-n-hexane, and then air dried to give 16 g of the object compound as white crystals (yield 84%).

Melting point : 145°–146° C. $^1$H-NMR (CDCl$_3$) δ ppm: 1.51 (s, 6H), 7.57 (dd, 4H), 9.0 (brs, 9H)

Reference Example 7

Preparation of 3-(4-chlorophenyl)-1-t-butoxycarbonyl-methyl-4, 5-dihydropyrazol-5-one To a suspension of 0.44 g (11 mmol) of 60% oily sodium hydride in 10 ml of anhydrous dimethylformamide was added dropwise a solution of 2.2 g (10 mmol) of 3-(4-chlorophenyl)-4, 5-dihydropyrazol-5-one in dimethylformamide (5 ml) at 0° C. After 30 minutes of stirring at room temperature, 2.1 g (11 mmol) of t-butyl bromoacetate was added dropwise, and stirring was continued for another 2 hours. To the reaction solution was added 50 ml of diethyl ether and 50 ml of water, and vigorously agitated. The resultant solution was separated, and the aqueous layer was extracted twice with 50 ml of diethyl ether. The organic layer was combined and washed successively with water and saturated brine solution, and dried over anhydrous sodium sulfate. Then the solvent was evaporated under reduced pressure. The obtained crude product was purified by silica gel column chromatography (n-hexane/ethyl acetate=4/1 (v/v)) to give 3.2 g of the object compound as a colorless oil (yield 95%).

$^1$H-NMR (CDCl$_3$) δ ppm: 1.45 (s, 3H), 1.49 (s, 6H), 4.39 (s, 2H), 7.48 (dd, 4H)

Example 33

Preparation of 1-phenyl-3-(4-methylphenyl)-4,5-dihydropyrazole-5-thione (Compound No. 33)

A mixture of 5.6 g (20 mmol) of 1-phenyl-3-(4-methylphenyl)-4, 5-dihydropyrazol-5-one, 6.1 g (15 mmol) of Lawesson's reagent and 50 ml of toluene was heated under reflux for 2 hours. The reaction solution was concentrated, and the residue was purified by silica gel column chromatography (n-hexane/ethyl acetate=10/1 (v/v)) and recrystallized from diethyl ether-n-hexane to give quantitatively 5.9 g of the object compound as pale yellow crystals.

Melting point : 112°–113° C. $^1$H-NMR (CDCl$_3$) δ ppm: 1.63 (s, 6H), 2.38 (s, 3H), 7.1–8.2 (m, 9H)

Similarly to Example 33 described above, various compounds (Compound No. 34 to Compound No. 62) shown in Table 2 below were obtained. Table 2 also shows the property of the compounds.

TABLE 2

| Compound No. | Xn | Ym | R$^2$ | R$^3$ | Property |
|---|---|---|---|---|---|
| 33 | 4-methoxy | hydrogen atom | Me | Me | mp: 112–113° C. |
| 34 | 3-chloro | hydrogen atom | Me | Me | mp: 89–91° C. |
| 35 | 4-chloro | hydrogen atom | Me | Me | mp: 102–103° C. |
| 36 | 3, 4-dichloro | hydrogen atom | Me | Me | mp: 104–106° C. |
| 37 | 4-fluoro | hydrogen atom | Me | Me | mp: 79–80° C. |
| 38 | 4-bromo | hydrogen atom | Me | Me | mp: 112–113° C. |
| 39 | 4-trifluoromethyl | hydrogen atom | Me | Me | mp: 107–108° C. |
| 40 | 4-isopropyl | hydrogen atom | Me | Me | mp: 102–103° C. |
| 41 | 4-n-butyl | hydrogen atom | Me | Me | yellow oil |
| 42 | 4-t-butyl | hydrogen atom | Me | Me | mp: 113–114° C. |
| 43 | 4-methoxy | hydrogen atom | Me | Me | mp: 67–69° C. |
| 44 | 4-n-butoxy | hydrogen atom | Me | Me | mp: 72–73° C. |

TABLE 2-continued

| Compound No. | Xn | Ym | R$^2$ | R$^3$ | Property |
|---|---|---|---|---|---|
| 45 | 4-methoxycarbonyl | hydrogen atom | Me | Me | mp: 98–99° C. |
| 46 | 4-n-propoxycarbonyl | hydrogen atom | Me | Me | mp: 55–56° C. |
| 47 | 4-t-butoxycarbonyl | hydrogen atom | Me | Me | mp: 125–127° C. |
| 48 | 4-nitro | hydrogen atom | Me | Me | mp: 122–124° C. |
| 49 | 4-phenyl | hydrogen atom | Me | Me | mp: 107–108° C. |
| 50 | hydrogen atom | 4-chloro | Me | Me | mp: 113–115° C. |
| 51 | 3-chloro | 4-chloro | Me | Me | mp: 121–122° C. |
| 52 | 4-chloro | 4-chloro | Me | Me | mp: 90–91° C. |
| 53 | 4-chloro | 4-bromo | Me | Me | mp: 102–103° C. |
| 54 | 4-chloro | 4-methyl | Me | Me | mp: 126–127° C. |
| 55 | 4-chloro | 4-methoxy | Me | Me | mp: 96–97° C. |
| 56 | 4-trifluoromethyl | 4-methoxy | Me | Me | mp: 107–108° C. |
| 57 | 4-chloro | hydrogen atom | Me | Et | yellow oil |
| 58 | 4-chloro | hydrogen atom | Me | n-Pr | mp: 83–85° C. |
| 59 | 4-chloro | hydrogen atom | Me | iso-Pr | mp: 81–82° C. |
| 60 | 4-chloro | hydrogen atom | Et | Et | mp: 66–68° C. |
| 61 | 4-chloro | hydrogen atom | —(CH$_2$)$_4$— | | mp: 115–117° C. |
| 62 | 4-chloro | hydrogen atom | —(CH$_2$)$_5$— | | mp: 106–107° C. |

Me: methyl, Et: ethyl, Pr: propyl

In the above Table 2, the compounds whose property is shown to be yellow oil have NMR spectra as indicated below.

$^1$H-NMR (CDCl$_3$) δ ppm;

Compound No. 41: 0.7–1.9 (m, 7H), 1.66 (s, 6H), 2.65 (t, 2H), 7.1–8.2 (m, 9H)

Compound No. 57: 0.60 (t, 3H), 1.60 (s, 6H), 2.15 (q, 2H), 7.1–8.2 (m, 9H)

Example 63

Preparation of 3-(4-chlorophenyl)-1-t-butoxycarbonylmethyl-4, 5-dihydropyrazol-5-thione (Compound No. 63)

A mixture of 1.0 g (3.0 mmol) of 3-(4-chlorophenyl)-1-t-butoxycarbonylmethyl-4, 5-dihydropyrazol-5-one, 0.90 g (2.2 mmol) of Lawesson's reagent and 10 ml of toluene was heated under reflux for 2 hours. The reaction solution was concentrated under reduced pressure and the residue was purified by silica gel column chromatography (n-hexane/ethyl acetate=10/1 (v/v)) to give 1.0 g the object compound as a yellow oil (yield 94%).

$^1$H-NMR (CDCl$_3$) δ ppm: 1.43 (s, 9H), 1.54 (s, 6H), 4.81 (s, 2H), 7.55 (dd, 4H)

Similarly to Example 63 described above, various compounds (Compound No. 64 to Compound No. 74) shown in Table 3 below were obtained. Table 3 also shows the property of the compounds.

TABLE 3

[Structure: X_n-phenyl group connected to C=N-N ring with R^2, R^3 substituents and C(R^5)(R^6)-(CH_2)_p-COOR^4 side chain, with S]

| Compound No. | Xn | $R^2$ | $R^3$ | $R^4$ | $R^5$ | $R^6$ | p | Property |
|---|---|---|---|---|---|---|---|---|
| 63 | 4-chloro | Me | Me | t-Bu | H | H | 0 | yellow oil |
| 64 | H | Me | Me | t-Bu | H | H | 0 | yellow oil |
| 65 | 4-chloro | Me | Me | Me | H | H | 0 | yellow oil |
| 66 | 4-chloro | Me | Me | iso-Pr | H | H | 0 | yellow oil |
| 67 | 4-chloro | Me | Me | n-Bu | H | H | 0 | yellow oil |
| 68 | 4-chloro | Me | Me | Ph | H | H | 0 | mm: 106–108° C. |
| 69 | 4-chloro | Me | Me | t-Bu | Me | H | 0 | mp: 77–78° C. |
| 70 | 4-chloro | Me | Me | Et | Me | Me | 0 | mp: 80–81° C. |
| 71 | 4-chloro | Me | Me | t-Bu | Me | Me | 0 | mp: 79–80° C. |
| 72 | 4-chloro | Me | Me | t-Bu | H | H | 1 | mp: 129–131° C. |
| 73 | 4-chloro | Me | Me | t-Bu | H | H | 2 | yellow oil |
| 74 | 4-chloro | Me | iso-Pr | t-Bu | H | H | 0 | yellow oil |

H: hydrogen atom, Me: methyl, Pr: propyl, Bu: butyl, Ph: phenyl

In the above Table 3, the compounds whose property is shown to be yellow oil have NMR spectra as indicated below.

$^1$H-NMR (CDCl$_3$) δ ppm;
Compound No 64: 1.43 (s, 9H), 1.53 (s, 6H), 4.88 (s, 2H), 7.1–7.6 (m, 3H), 7.7–8.0 (m, 2H)
Compound No 65: 1.56 (s, 6H), 3.24 (s, 3H), 4.94 (s, 2H), 7.56 (dd, 4H)
Compound No 66 : 1.23 (d, 6H), 1.55 (s, 6H), 4.88 (s, 2H), 4.9–5.3 (m, 1H), 7.57 (dd, 4H)
Compound No 67 : 0.7–1.9 (m, 7H), 1.56 (s, 6H), 4.15 (t, 2H), 4.93 (s, 2H), 7.56 (dd, 4H)
Compound No 73: 1 43 (s, 9H), 1.52 (s, 6H), 2.0–2.5 (m, 4H), 4.20 (t, 2H), 7.53 (dd, 4H)
Compound No 74: 0.80 (d, 3H), 1.00 (d, 3H), 1.43 (s, 9H), 1.55 (s, 6H), 1.9–2.6 (m, 1H), 4.91 (s, 2H), 7.55 (dd, 4H)

Reference Example 8

Synthesis of 3-(2-pyridyl)-4, 5-dihydropyrazol-5-one (intermediate)

A mixture of 2.8 g (12.7 mmol) of ethyl α-(4-chlorobenzoyl)isobutyrate, 1.6 g (32.0 mmol) of hydrazine monohydrate, and 20 ml of ethanol was heated under reflux for 18 hours. The reaction solution was concentrated under reduced pressure. The obtained crude product was washed with n-hexane - diethyl ether mixture and dried under reduced pressure to give 2.0 g of the object compound as white crystals (yield 82%).

Melting point : 135°–136° C. $^1$H-NMR (CDCl$_3$) δ ppm 1.59 (s, 6H), 7.08–7.40 (m, 1H), 7.50–8.22 (m, 1H), 8.47–8.63 (m, 1H)

Reference Example 9

Synthesis of 3-(2-pyridyl)-1-propyl-4, 5-dihydropyrazol-5-one (intermediate)

To a suspension of 0.29 g (7.3 mmol) of 60% oily sodium hydride in 10 ml of anhydrous dimethylformamide was added dropwise a solution of 1.2 g (6.2 mmol) of 3-(2-pyridyl)-4, 5-dihydropyrazol-5-one in dimethylformamide (10 ml) at 0° C. After one hour of stirring at room temperature, 0.92 g (7.5 mmol) of 1-bromopropane was added dropwise and stirring was continued for another 18 hours. To the reaction solution was added 50 ml of diethyl ether and 50 ml of water, and vigorously agitated. The resultant solution was separated, and the aqueous layer was extracted twice with 50 ml of ethyl acetate. The organic layer was combined and washed successively with water and saturated brine solution, and dried over anhydrous sodium sulfate. Then the solvent was evaporated under reduced pressure. The obtained crude product was purified by silica gel column chromatography (n-hexane/ethyl acetate=4/1 (v/v)) to give 1.4 g of the object compound as a colorless oil (yield 96%).

$^1$H-NMR (CDCl$_3$) δ ppm: 0.95 (t, 3H), 1.40–2.15 (m, 2H), 1.56 (s, 6H), 3.72 (t, 2H), 7.08–8.09 (m, 3H), 8.49–8.65 (m, 1H)

Reference Example 10

Synthesis of 3-(3-pyridyl)-1-phenyl-4, 5-dihydropyrazol-5-one (intermediate)

A mixture of 1.5 g (6.8 mmol) of ethyl α-(3-pyridylcarbonyl)isobutyrate and 0.88 g (12 mmol) of phenyl hydrazine was dissolved in 50 ml of toluene, and the solution was dehydrated and heated under reflux in the presence of p-toluenesulfonic acid monohydrate (catalytic amount) for 18 hours. The reaction solution was concentrated under reduced pressure, and the residue was purified by silica gel column chromatography (n-hexane/ethyl acetate=3/2 (v/v)) to give 1.5 g of the object compound as white crystals (yield 83%).

Melting point: 102°–103° C. $^1$H-NMR (CDCl$_3$) δ ppm: 1.59 (s, 6H), 7.12–7.65 (m, 4H), 7.88–8.22 (m, 4H), 9.00–9.15 (m, 1H)

Example 75

Preparation of 3-(3-pyridyl)-1-phenyl-4, 5-dihydropyrazole-5-thione

A mixture of 1.2 g (4.5 mmol) of 3-(3-pyridyl)-1-phenyl-4, 5-dihydropyrazol-5-one, 1.4 g (3.4 mmol) of Lawesson's reagent and 10 ml of toluene was heated under reflux for 2 hours. The reaction mixture was concentrated under reduced pressure. The residue was purified by silica gel column chromatography (n-hexane/ethyl acetate=3/2 (v/v)) and recrystallized from ethanol to give 1.0 g of 3-(3-pyridyl)-1-phenyl-4, 5-dihydropyrazole-5-thione.

Similarly to Reference Examples 8 to 10 and Example 75 described above, various compounds shown in Tables 4 to 8 below were obtained by employing appropriate starting materials.

TABLE 4

Compound of Example 75

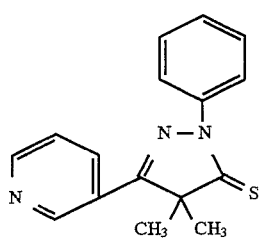

Melting point: 132–133° C.
¹H-NMR(CDCl₃)δ ppm:
1.67(s, 6H), 7.19–7.67(m, 4H),
7.82–8.35(m, 3H), 8.59–8.75
(m, 1H), 9.09–9.22(m, 1H)

Compound of Example 76

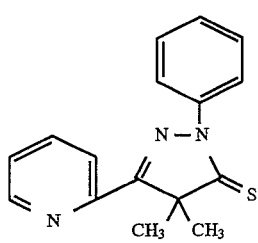

Melting point: 90–91° C.
¹H-NMR(CDCl₃)δ ppm:
1.75(s, 6H), 7.10–8.25(m, 8H),
8.50–8.70(m, 1H)

Compound of Example 77

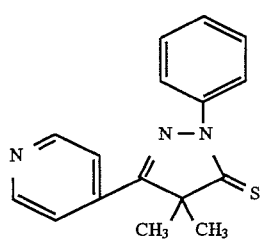

Melting point: 137–139° C.
¹H-NMR(CDCl₃)δ ppm:
1.55(s, 6H), 7.25–7.68(m, 3H),
7.66–7.85(m, 2H), 7.90–8.12
(m, 2H), 8.15–8.83(m, 2H)

Compound of Example 78

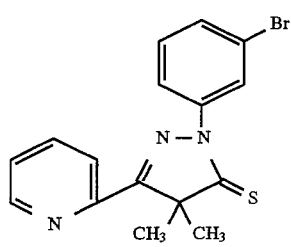

Melting point: 142–143° C.
¹H-NMR(CDCl₃)δ ppm:
1.74(s, 6H), 7.09–8.17(m, 7H),
8.46–8.64(m, 1H)

Compound of Example 79

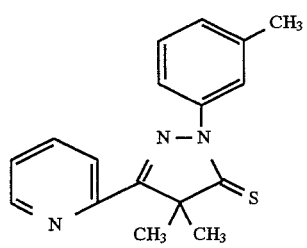

Melting point: 93–94° C.
¹H-NMR(CDCl₃)δ ppm:
1.73(s, 6H), 2.38(s, 3H), 7.10–
7.38(m, 3H), 7.50–8.20(m, 4H),
8.49–8.65(m, 1H)

TABLE 5

Compound of Example 80

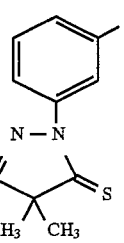

Yellow oil
¹H-NMR(CDCl₃)δ ppm:
1.27(d, 6H), 1.76(s, 6H),
2.70–3.25(m, 1H), 7.20–
7.45(m, 3H), 7.60–8.30
(m, 4H), 8.50–8.70(m,
1H)

Compound of Example 81

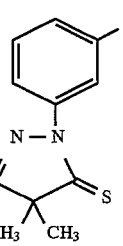

Melting point:
86–88° C.
¹H-NMR(CDCl₃)δ ppm:
1.76(s, 6H), 7.20–8.75
(m, 8H)

Compound of Example 82

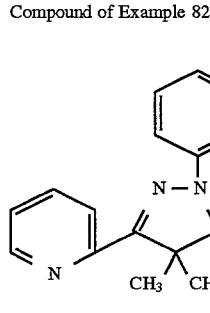

Melting point:
113–114° C.
¹H-NMR(CDCl₃)δ ppm:
1.70(s, 6H), 3.77(s, 3H),
6.71–7.31(m, 3H), 7.48–
8.20(m, 4H), 8.50–8.70
(m, 1H)

Compound of Example 83

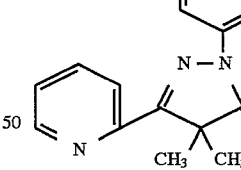

Melting point:
185–186° C.
¹H-NMR(CDCl₃)δ ppm:
1.78(s, 6H), 7.24–8.78
(m, 8H)

Compound of Example 84

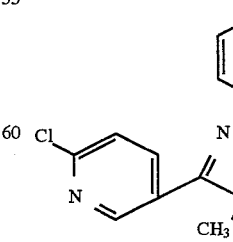

Melting point:
79–80° C.
¹H-NMR(CDCl₃)δ ppm:
1.64(s, 6H), 7.18–7.74(m,
4H), 7.89–8.32(m, 3H),
9.01(d, 1H)

TABLE 6

Compound of Example 85

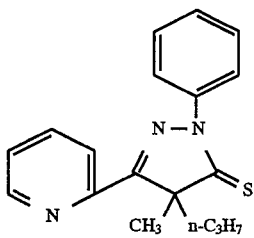

Melting point: 83–85° C.
1H-NMR (CDCl3)δ ppm:
0.50–1.40(m, 5H), 1.72(s, 3H),
1.80–2.95(m, 2H), 7.15–8.25
(m, 8H), 8.50–8.70(m, 1H)

Compound of Example 86

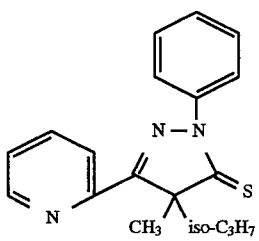

Property: Yellow oil
1H-NMR(CDCl3)δ ppm:
0.85(d, 3H), 1.10(d, 3H), 1.84
(s, 3H), 2.40–3.05(m, 1H),
7.05–8.20(m, 8H), 8.44–8.63
(m, 1H)

Compound of Example 87

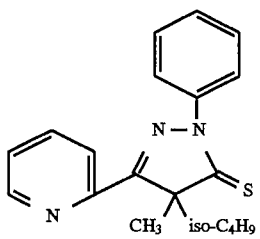

Property: Yellow oil
1H-NMR(CDCl3)δ ppm:
0.70(dd, 6H), 1.08–1.65(m, 1H),
1.70(s, 3H), 1.93–2.95(m, 2H),
7.12–8.28(m, 8H), 8.53–8.73
(m, 1H)

Compound of Example 88

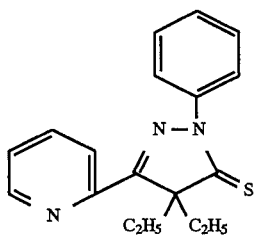

Melting point: 77–79° C.
1H-NMR(CDCl3)δ ppm:
0.59(t, 6H), 1.80–2.95(m, 4H),
7.15–8.30(m, 8H), 8.50–8.70
(m, 1H)

Compound of Example 89

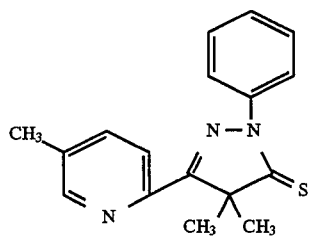

Melting Point: 113–114° C.
1H-NMR(CDCl3)δ ppm:
1.75(s, 6H), 2.38(s, 3H),
7.30–7.63(m, 4H), 7.90–8.20
(m, 3H), 8.40–8.51(m, 1H)

TABLE 7

Compound of Example 90

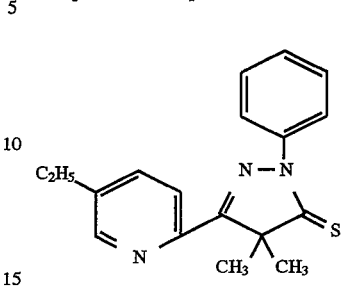

Melting point: 91–93° C.
1H-NMR(CDCl3)δ ppm:
1.26(t, 3H), 1.75(s, 6H), 2.18
(q, 2H), 7.27–7.62(m, 4H),
7.92–8.15(m, 3H), 8.38–8.55
(m, 1H)

Compound of Example 91

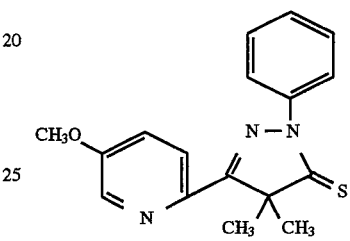

Melting point: 98–99° C.
1H-NMR(CDCl3)δ ppm:
1.72(s, 6H), 3.85(s, 3H),
7.04–7.60(m, 4H), 7.90–8.16
(m, 3H), 8.26(d, 1H)

Compound of Example 92

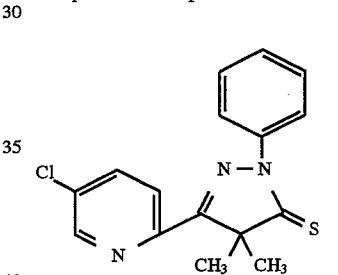

Melting point: 108–109° C.
1H-NMR(CDCl3)δ ppm:
1.72(s, 6H), 7.20–8.25(m, 7H),
8.55–8.65(m, 1H)

Compound of Example 93

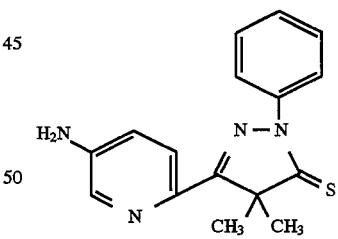

Melting point: 130–131° C.
1H-NMR(CDCl3)δ ppm:
1.72(s, 6H), 3.78–4.14(m, 2H),
6.70–7.65(m, 4H), 7.80–8.25
(m, 4H)

Compound of Example 94

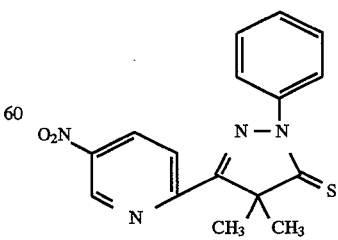

Melting point: 168–169° C.
1H-NMR(CDCl3)δ ppm:
1.72(s, 6H), 7.20–7.70(m, 3H),
7.75–8.16(m, 2H), 8.17–8.65
(m, 2H), 9.32–9.53(m, 1H)

TABLE 8

Compound of Example 95

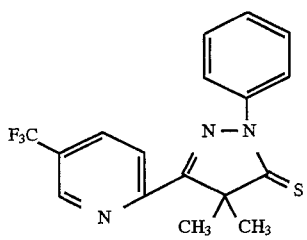

Melting point: 93–95° C.
$^1$H-NMR(CDCl$_3$)δ ppm:
1.72(s, 6H), 7.25–7.70(m, 3H),
7.75–8.30(m, 4H), 8.65–8.75
(m, 1H)

Compound of Example 96

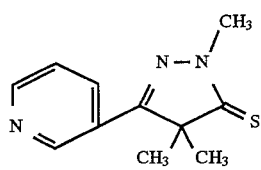

Melting point: 88–90° C.
$^1$H-NMR(CDCl$_3$)δ ppm:
1.56(s, 6H), 3.75(s, 3H),
7.20–7.49(m, 1H), 8.02–8.28
(m, 1H), 8.56–8.75(m, 1H),
9.02–9.18(m, 1H)

Compound of Example 97

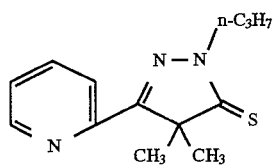

Property: Yellow oil
$^1$H-NMR(CDCl$_3$)δ ppm:
0.98(t, 3H), 1.62(s, 6H),
1.50–2.30(m, 2H), 4.15(t, 2H),
7.10–8.15(m, 3H), 8.45–8.65
(m, 1H)

Compound of Example 98

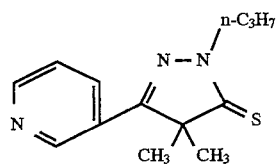

Property: Yellow oil
$^1$H-NMR(CDCl$_3$)δ ppm:
0.98(t, 3H), 1.53(s, 6H),
1.68–2.15(m, 2H), 4.14(t, 2H),
7.21–7.50(m, 1H), 8.04–8.30
(m, 1H), 8.57–8.75(m, 1H),
9.02–9.18(m, 1H)

Compound of Example 99

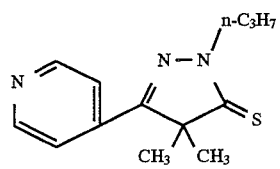

Property: Yellow oil
$^1$H-NMR(CDCl$_3$)δ ppm:
0.96(t, 3H), 1.53(s, 6H),
1.69–2.22(m, 2H), 4.14(t, 2H),
7.67(dd, 2H), 8.65(dd, 2H)

Test Example 1 Test on *Tetranychus urticae* Koch

The compound of the present invention was dissolved in 1 ml of acetone and diluted to a specific concentration with an aqueous solution containing 0.01% of an emulsifier (Tween 80, product of Atlas Co., Ltd.). Pieces of kidney bean (*Phaseolus vulgaris*) leaf were placed on agar gel and female imagos of *Tetranychus urticae* Koch were inoculated thereto, and the above prepared solution was scattered. Two days after, the mortality of the mites was evaluated. The results are shown in Table 9. Test Compound Nos. shown in Table 9 correspond to Compound Nos. shown in Table 1. In Table 9, Compound A is 3-(4-chlorophenyl)-1-propyl-4, 5-dihydropyrazol-5-one obtained by Reference Example 2.

TABLE 9

| Test Compound No. | Concentration of Test Compound (ppm) | Mortality of mites (%) |
|---|---|---|
| 1 | 400 | 100 |
| 4 | 400 | 100 |
| 6 | 400 | 100 |
| 7 | 400 | 100 |
| 14 | 400 | 100 |
| 17 | 400 | 100 |
| 19 | 400 | 100 |
| 21 | 400 | 100 |
| 27 | 400 | 100 |
| 31 | 400 | 100 |
| Compound A | 400 | 0 |

Test Example 2 Test on *Panaonychus citri* McGregor

The compound of the present invention was dissolved in 1 ml of acetone and diluted to a specific concentration with an aqueous solution containing 0.01% of an emulsifier (Tween 80, product of Atlas Co., Ltd.). Pieces of orange (*Citrus unshiu* Marcov) leaf were placed on agar gel and female imagos of *Panaonychus citri* McGregor were inoculated thereto, and the above prepared solution was scattered. Two days after, the mortality of the mites was evaluated. The results are shown in Table 10. Test Compound Nos. shown in Table 10 correspond to Compound Nos. shown in Table 1.

TABLE 10

| Test Compound No. | Concentration of Test Compound (ppm) | Mortality of mites (%) |
|---|---|---|
| 1 | 400 | 100 |
| 4 | 400 | 100 |
| 6 | 400 | 100 |
| 7 | 400 | 100 |
| 11 | 400 | 100 |
| 14 | 400 | 100 |
| 17 | 400 | 100 |
| 19 | 400 | 100 |
| 29 | 400 | 100 |
| 30 | 400 | 100 |
| 31 | 400 | 100 |
| Compound A | 400 | 0 |

Test Example 3 Test on *Tetranychus urticae* Koch

The compound of the present invention was dissolved in 1 ml of acetone and diluted to a specific concentration with an aqueous solution containing 0.01% of an emulsifier (Tween 80, product of Atlas Co., Ltd.). Pieces of kidney bean (*Phaseolus vulgaris*) leaf were placed on agar gel and female imagos of *Tetranychus urticae* Koch were inoculated thereto, and the above prepared solution was scattered. Two days after, the mortality of the mites was evaluated. The results are shown in Table 11. Test Compound Nos. shown in Table 11 correspond to Compound Nos. shown in Tables 2 and 3. In Table 11, Compound B is 1-phenyl-3-(4-methylphenyl)-4, 5-dihydropyrazol-5-one obtained by Reference Example 5 and Compound C is 3-(4-chlorophenyl)-1-t-butoxycarbonyl-methyl-4, 5-dihydropyrazol-5-one obtained by Reference Example 7.

TABLE 11

| Test Compound No. | Concentration of Test Compound (ppm) | Mortality of mites (%) |
|---|---|---|
| 35 | 400 | 100 |
| 37 | 400 | 100 |
| 39 | 400 | 100 |
| 42 | 400 | 100 |
| 44 | 400 | 100 |
| 48 | 400 | 100 |
| 52 | 400 | 100 |
| 55 | 400 | 100 |
| 57 | 400 | 100 |
| 59 | 400 | 100 |
| 63 | 400 | 100 |
| 66 | 400 | 100 |
| 69 | 400 | 100 |
| 71 | 400 | 100 |
| 72 | 400 | 100 |
| 73 | 400 | 100 |
| 74 | 400 | 100 |
| Compound B | 400 | 0 |
| Compound C | 400 | 0 |

Test Example 4 Test on *Panaonychus citri* McGregor

The compound of the present invention was dissolved in 1 ml of acetone and diluted to a specific concentration with an aqueous solution containing 0.01% of an emulsifier (Tween 80, product of Atlas Co., Ltd.). Pieces of orange (*Citrus unshiu* Marcov) leaf were placed on agar gel and female imagos of *Panonychus citri* McGregor were inoculated thereto, and the above prepared solution was scattered. Two days after, the mortality of the mites was evaluated. The results are shown in Table 12. Test Compound Nos. shown in Table 12 correspond to Compound Nos. shown in Tables 2 and 3.

TABLE 12

| Test Compound No. | Concentration of Test Compound (ppm) | Mortality of mites (%) |
|---|---|---|
| 35 | 400 | 100 |
| 38 | 400 | 100 |
| 39 | 400 | 100 |
| 42 | 400 | 100 |
| 43 | 400 | 100 |
| 48 | 400 | 100 |
| 55 | 400 | 100 |
| 56 | 400 | 100 |
| 59 | 400 | 100 |
| 64 | 400 | 100 |
| 67 | 400 | 100 |
| 69 | 400 | 100 |
| 71 | 400 | 100 |
| 72 | 400 | 100 |
| 73 | 400 | 100 |
| 74 | 400 | 100 |
| Compound B | 400 | 0 |
| Compound C | 400 | 0 |

Test Example 5 Test on *Tetranychus urticae* Koch

The compound of the present invention (2 parts by weight) was dissolved in acetone (98 parts by weight) and diluted to a concentration of 300 ppm with an aqueous solution containing 0.04% of a spreading agent (product of Nihon Noyaku Co., Ltd. trademark, Shin-Linoh). Imagos of *Tetranychs urticae* Koch were inoculated to kidney bean (*Phaseolus vulgaris*) planted in pots and the above prepared solution was sprayed onto the plant until the leaves were dripping. Two days after, the mortality of the mites was evaluated. The results are shown in Table 13. Test Compound Nos. shown in Table 13 correspond to the compounds prepared by the same Example Nos. Similarly, Test Compound Nos. shown in Table 14 correspond to the compounds prepared by the same Example Nos.

TABLE 13

| Test Compound No. | Mortality of mites (%) |
|---|---|
| 75 | 100 |
| 77 | 100 |
| 78 | 100 |
| 81 | 100 |
| 82 | 100 |
| 85 | 100 |
| 87 | 100 |
| 88 | 100 |
| 89 | 100 |
| 92 | 100 |
| 93 | 100 |
| 94 | 100 |
| 95 | 100 |

Test Example 6 Test on *Panonychus citri* McGregor

The compound of the present invention (2 parts by weight) was dissolved in acetone (98 parts by weight) and diluted to a concentration of 300 ppm with an aqueous solution containing 0.04% of a spreading agent (product of Nihon Noyaku Co., Ltd. trademark, Shin-Linoh). Imagos of *Panonychus citri* McGregor were inoculated to kidney bean (*Phaseolus vulgaris*) planted in pots and the above prepared solution was sprayed onto the plant until the leaves were dripping. Two days after, the mortality of the mites was evaluated. The results are shown in Table 14.

TABLE 14

| Test Compound No. | Mortality of mites (%) |
|---|---|
| 75 | 100 |
| 77 | 100 |
| 78 | 100 |
| 81 | 100 |
| 82 | 100 |
| 85 | 100 |
| 87 | 100 |
| 88 | 100 |
| 89 | 100 |
| 92 | 100 |
| 93 | 100 |
| 94 | 100 |
| 95 | 100 |

We claim:

1. A 4, 5-dihydropyrazole-5-thione derivative represented by the general formula

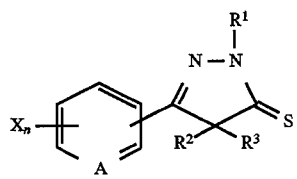

wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group which may have substituents, a phenylcarbonyl lower alkyl group, a lower alkylcarbonyl lower alkyl group, a group or a group

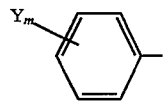

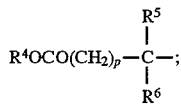

in which Y represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; m is 0 or an integer of 1 to 3; $R^4$ represents a lower alkyl group; p is 0, 1 or 2; $R^5$ and $R^6$ are the same or different and represent a hydrogen atom or a lower alkyl group; $R^2$ and $R^3$ are the same or different and represent a lower alkyl group or a cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, a cyano group, an amino group or a nitro group; n is 0 or an integer of 1 to 3; A represents —(C)— or —(N)—; and the substituent contained in the abovementioned benzyl group, phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

2. A 4, 5-dihydropyrazole-5-thione derivative represented by the general formula

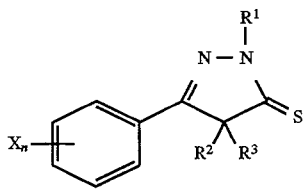

wherein $R^1$ represents a straight- or branched-chain alkyl group having 1 to 12 carbon atoms, a cycloalkyl group having 3 to 8 carbon atoms, a lower alkenyl group, a lower alkynyl group, a benzyl group which may have substituents, a phenylcarbonyl lower alkyl group or a lower alkylcarbonyl lower alkyl group; $R^2$ and $R^3$ are the same or different and represent a lower alkyl group or a cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a phenoxy group which may have substituents, a phenyl group which may have substituents, a cyano group or a nitro group; n is 0 or an integer of 1 to 3; and the substituent contained in the abovementioned benzyl group, phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

3. A 4, 5-dihydropyrazole-5-thione derivative represented by the general formula

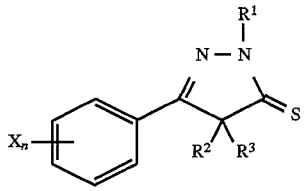

wherein $R^1$ represents a group

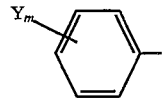

or a group

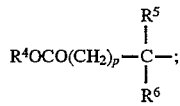

in which Y represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; m is 0 or an integer of 1 to 3; $R^4$ represents a lower alkyl group; p is 0, 1 or 2; $R^5$ and $R^6$ are the same or different and represent a hydrogen atom or a lower alkyl group; $R^2$ and $R^3$ are the same or different and represent a lower alkyl group or a lower cycloalkyl group having 3 to 8 carbon atoms, or $R^2$ and $R^3$ may be combined to form a cycloalkyl ring having 3 to 8 carbon atoms; X represents a halogen atom, a lower alkyl group, a lower alkoxy group, a lower haloalkyl group, a lower haloalkoxy group, a lower alkoxycarbonyl group, a phenoxy group which may have substituents, a phenyl group which may have substituents, an amino group, a cyano group or a nitro group; n is 0 or an integer of 1 to 3; and the substituent contained in the above-mentioned phenoxy group and phenyl group which may have substituents is at least one group selected from the group consisting of a halogen atom, a lower alkyl group, a lower alkoxy group, a lower haloalkyl group, a nitro group, a cyano group and a lower alkoxycarbonyl group.

4. A 4, 5-dihydropyrazole-5-thione derivative represented by the general formula

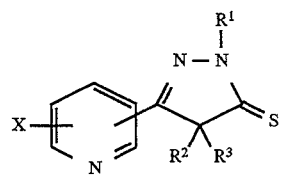

wherein $R^1$ represents a phenyl group which may have substituents selected from the group consisting of a halogen atom, a lower alkyl group, a lower alkoxy group, a lower haloalkyl group and a nitro group or a lower alkyl group; $R^2$ and $R^3$ each represent a lower alkyl group; and X represents a hydrogen atom, a halogen atom, a lower alkyl group, a lower alkoxy group, a lower haloalkyl group, an amino group or a nitro group.

5. A miticide composition comprising the 4, 5-dihydropyrazole-5-thione derivative according to claim 1 as an active ingredient.

* * * * *